United States Patent [19]

Roughton et al.

[11] 3,946,309

[45] Mar. 23, 1976

[54] CELL FOR MEASURING ELECTRICAL RESISTIVITY OF A LIQUID

[76] Inventors: Charles Lyn Roughton, 12 Cedar Grove, Hinderton Road, Neston, Wirral; Christopher Ian Arthur Ellis, 30 Hill Road, Birkenhead, Cheshire, both of England

[22] Filed: Aug. 22, 1974

[21] Appl. No.: 499,598

Related U.S. Application Data

[63] Continuation of Ser. No. 277,608, Aug. 3, 1972, abandoned.

[52] U.S. Cl.................................. 324/64; 324/30 R
[51] Int. Cl.[2].................. G01R 27/14; G01N 27/42
[58] Field of Search............................ 324/30 R, 64

[56] References Cited
UNITED STATES PATENTS

| | | | |
|---|---|---|---|
| 2,832,734 | 4/1958 | Eckfeldt............................ | 324/30 X |
| 2,871,446 | 1/1959 | Wann................................. | 324/64 |
| 3,358,223 | 12/1967 | Birnstingl.............................. | 324/30 |
| 3,382,434 | 5/1968 | Gibson, Jr............................. | 324/64 |
| 3,443,222 | 5/1969 | Mildwater............................ | 324/64 |
| 3,566,233 | 2/1971 | Kahn................................. | 324/64 X |

OTHER PUBLICATIONS

C. M. Boyd, G. W. Johnson, "Studying Zooplankton Populations..." *Trans. Applns, Sea Going Computers Symp.* (Marine Techn. Soc. America) 1968.

*Primary Examiner*—R. V. Rolinec
*Assistant Examiner*—R. Hille
*Attorney, Agent, or Firm*—Diller, Brown, Ramik & Wight

[57] ABSTRACT

A cell for measuring the electrical resistivity of a liquid contains four aligned and linearly spaced electrodes. A current source is connected to the end electrodes and an amplifier is connected directly to the inner electrodes. The amplifier has a high input impedance characteristic sufficient to limit the current carried by the inner electrodes to a small value which renders it essentially independent of any fouling of the inner electrodes. The amplifier is connected to the current source to control the current output thereof so as to maintain a constant predetermined voltage drop across the inner electrodes whereby the output of the amplifier is independent of any IR drop due to the fouling of the outer electrodes. A reference and a measuring cell may each be connected as above with the high input impedance amplifier of the measuring cell controlling the current sources for both cells and the corresponding amplifier of the reference cell driving a suitable output indicator.

6 Claims, 5 Drawing Figures

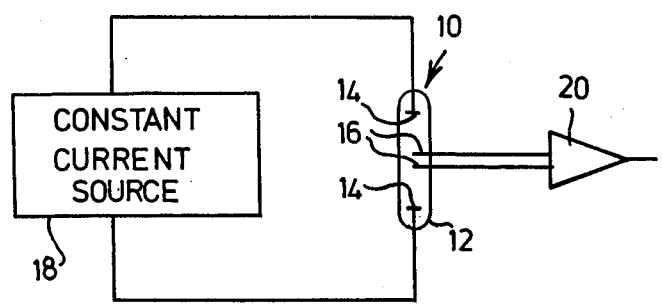
FIG. 1.
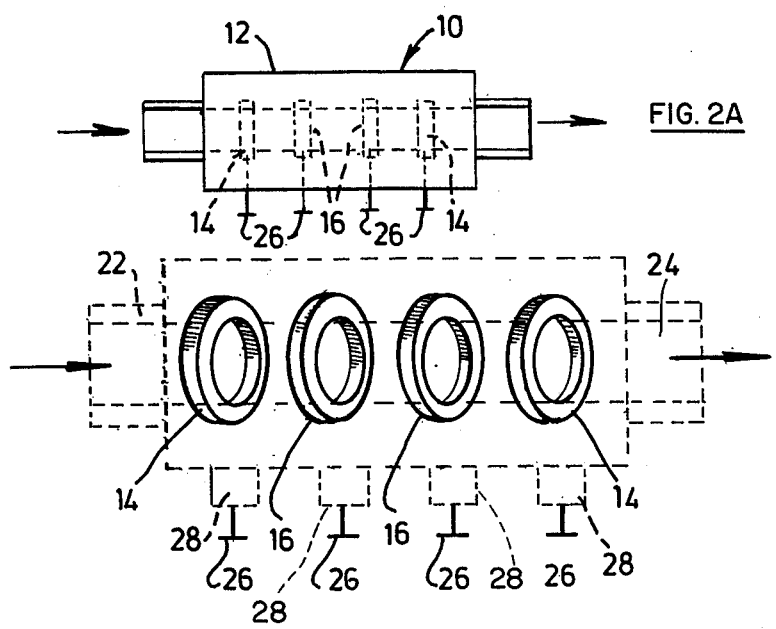
FIG. 2A
FIG. 2B

CELL FOR MEASURING ELECTRICAL RESISTIVITY OF A LIQUID

CROSS REFERENCE TO RELATED APPLICATION

This is a continuation of application Ser. No. 277,608 filed Aug. 3, 1972 and now abandoned.

The present invention relates to an improved cell for measuring the electrical conductivity of a liquor sample and also to a method of measuring the electrical conductivity of the sample.

It has previously been proposed to continuously sample the electrolytic content of a laundry wash liquor in order to use the information derived from the state of the liquor to formulate and control the wash and rinse programs. Alkali and various cleansing agents are added during the wash cycle and removed during the rinsing cycle. A minimum concentration of alkali must be present during the wash cycle in order to maintain adequate suspending power of the wash liquor. The concentration of alkali at the end of the rinsing cycle must be known to precise limits as an excess of alkali at the final rinse will cause galling which will necessitate expensive reprocessing. It becomes essential therefore to remove the alkali concentration from the wash and rinse liquors.

Previously the measurement of the alkalinity was accomplished by providing a cell having a pair of electrodes, disposed in the washing vessel, which are in intimate contact with the wash and rinse liquors being sampled. A voltage was applied to the electrodes, the value of the current then flowing in circuit connected to the two electrodes, after suitable temperature compensation, being an indication of the electrical conductivity and therefore the alkalinity of the wash liquor, since alkalinity is proportional to conductivity.

A major disadvantage with conductivity cells containing two electrodes is that, in general, after a period of operation, the electrodes become fouled and therefore the current flowing between them is reduced, giving a false conductivity and therefore alkalinity reading. In consequence, in order to obtain accurate reading from the cell, frequent cleaning is necessary.

The above problem is not restricted to the commercial laundry since conductivity measurement is of prime importance in other fields for example in the effluent and sewage fields where it is often desirable to measure the dissolved solids content prior to discharging into a river or sewer. Conductivity is of importance in the dyeing and textile cleansing process for the monitoring and control of processes.

According to the present invention there is provided a cell for measuring the electrical conductivity of a liquor sample which cell comprises a housing for containing the liquor sample and having four linearly-aligned electrodes disposed therein, the outer pair of electrodes being arranged for connection to a constant current source and the inner pair of electrodes being arranged for connection to the input terminals of high impedance amplifier, the voltage appearing across the inner electrodes being a measure of the electrical resistivity of the liquor sample, which is inversely proportional to the conductivity.

Also according to the present invention there is provided a method of measuring the electrical conductivity of a liquor sample which comprises introducing the liquor into a cell having four linearly-aligned electrodes disposed therein, passing a constant current through the outer pairs of electrodes and measuring the voltage across the inner pair of electrodes by means of a high input impedance amplifier to derive a signal indicative of the electrical resistivity of the liquor sample which is inversely proportional to the conductivity.

According to a further aspect of the invention there is provided a method of comparing the electrical conductivity of two liquor samples comprising introducing the samples into respective cells each including four linearly-aligned electrodes, applying an identical constant current to the outer electrodes of each of the cells, measuring the voltage across the inner electrodes of both cells by means of respective high input impedance amplifiers, varying the constant current in dependence upon the voltage measured across the inner part of electrodes of one of the cells to maintain the voltage across the latter pair of electrodes at a constant predetermined value and comparing the output voltages of the high input impedance amplifiers to provide a signal indicative of the difference in conductivities between the liquor samples.

The invention will now be further described by way of example with reference to the accompanying drawings in which:

FIG. 1 illustrates a control circuit embodying a cell in accordance with the present invention, FIGS. 2a and 2b illustrates one manner of laying out the electrodes in the cell and FIG. 3 illustrates the use of a two cell arrangement necessary to control and formulate the washing and rinsing cycles within a laundry washing vessel.

Figure 3:
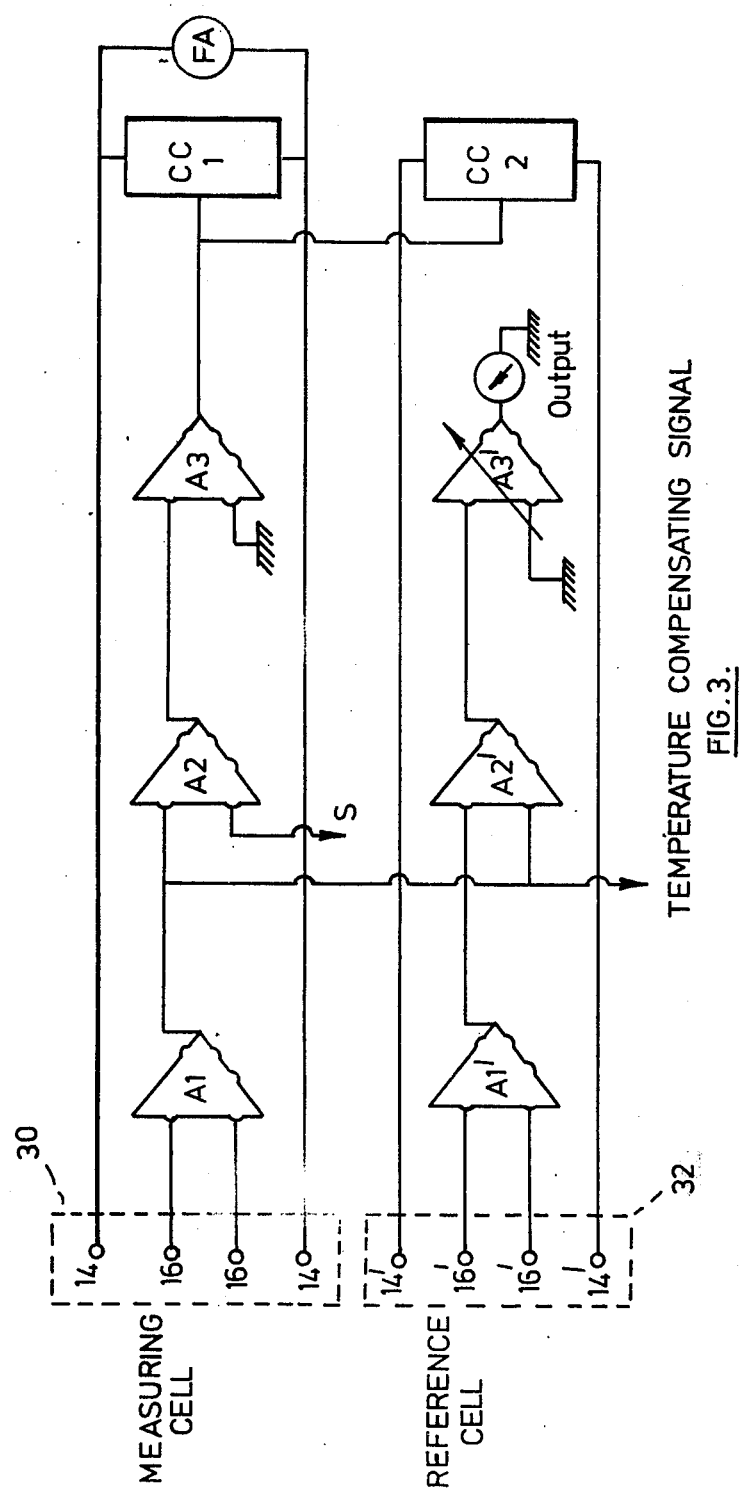

Referring to FIG. 1 a cell constructed in accordance with the present invention is shown generally as 10. It includes a housing 12 having two pairs of linearly-aligned electrodes 14 and 16 disposed therein. The outer electrodes are connected to a constant alternating current source 18 which serves to pass a constant current through the liquor sample contained in the housing 12. Conveniently the frequency of the constant current source is 1kHz. Electrodes 16 are connected to the input terminals of a high input impedance amplifier 20.

In practice, when a voltage is applied to the outer terminals 14, a constant current is caused to flow through the liquor sample contained in the housing 12. The amplifier 20 monitors the potential drop across the liquor sample between the two inner electrodes 16. This potential drop is an inverse function of the conductivity of the liquor sample. In view of the high input impedance of the amplifier the inner electrodes 16 carry only a very small current and therefore the potential drop across the electrodes 16 is substantially independent of any fouling of the inner electrodes.

Fouling of the outer electrodes does occur however and causes the voltage across them to rise since the current remains constant. This increase in voltage may be used to indicate the state of fouling of the outer electrodes. Providing the fouling is insufficient to affect the performance of the constant current source the signal from the inner electrodes is sensibly independent of fouling.

Should the fouling be such as to affect the performance of the constant current source, the voltage across the outer electrodes becomes excessive and may be used to give warning of the necessity for cleaning the electrodes. When the cell is used to measure the alkalinity of the liquor in a laundry washing machine for example, the increase in voltage may be used to operate a voltage level device to trigger a visible or audible alarm to shut down the laundry machine.

During the process it is necessary to compare the electrolytic content of the mains water supply with that of the sample being monitored within the washing vessel. More particularly, during the rinsing cycle, the purpose is to reduce the dissolved solids content of the rinsing liquor to a level which does not exceed that of the incoming mains water by more than a predetermined amount. The reason for this is that the electrolytic content of the mains water varies considerably over short durations of time and in different locations and it is therefore only by comparing the readings obtained from the two cells that it is possible to determine the excess solids content or alkalinity of the liquor sample within the washing vessel.

Referring to FIG. 2a and 2b it will be seen that the preferred layout of the cells consists of a cylindrical housing 12, having four annular electrodes 14,16, mounted therein. Inlet and exit ports 22 and 24 respectively are located in axial alignment with longitudinal axis of the housing and allow the liquor to be sampled to be introduced into the cell for sampling and removed therefrom after sampling. A suitable electrical connection 26, is made to each electrode, the connections passing through the housing 12 and terminating on an insulating block 28.

Whilst the following description of FIG. 3 is with respect to washing and rinsing cycles of a laundry washing process, as has been previously mentioned, the cells and methods of the present invention may be put to other applications involving the measurement and control of electrical conductivity where two cells have to be employed and where one cell is used as a reference to show the difference in electrolytic content of the sampling cell.

In FIG. 3 the inner electrodes of a first measuring cell 30 are connected to the input terminals of a high input impedance unity gain amplifier A1 whose output is fed to one input terminal of a differential amplifier A2. A reference signal S comprising the constant current supply to the circuit is fed to the other input terminal of the amplifier A2. This signal may conveniently be at 1kHz. The output of amplifier A2 is fed to the input of a high gain amplifier A3 whose output controls the magnitude of the "constant" current fed by a constant current control circuit C.C.1 to electrodes 14 of cell 30.

This constant current, which is sensibly independent of the cell resistance, is fed to the cell 30 and will adjust so that the voltage across electrodes 16 remains sensibly constant in spite of changes in the conductivity of the cell liquor. The circuit required to maintain the voltage across the electrodes 16 constant will be dependent on the conductivity of the cell liquor. A second constant current of equal magnitude to that applied to cell 30 is also applied to the constant current control circuit C.C.2 of cell 32 by amplifier A.3. Cell 30 contains the wash liquor and cell 32 the mains or other water used for rinsing or as a reference. Amplifier A1' is similar to amplifier A1 and its output is fed to the differential or subtractive amplifier A2'. The output of amplifier A1 is fed to the other input of amplifier A2' so that the difference signal, suitably amplified, appears at the output of amplifier A2'. The output of this amplifier depends on the difference in conductivity of the cell 30 liquor over that of the rinsing water or reference sample in cell 32. Normally of course the conductivity of the liquor in cell 30 will be greater than that in cell 32. The output of amplifier A2' is fed to the input of amplifier A3' which may conveniently be given a variable gain characteristic, thus enabling the range of measurement to be increased to any desired extent. This output may be used to control the number of rinses required to produce the desired rinse quality.

This dual cell arrangement, or suitable modification, may also be used to control the dispensing of alkali in the washing cycle.

In each of the foregoing arrangements corrections for changes of temperature of the liquor must be made. Compensating techniques for temperature correction are available for example by use of thermistors. Thermistors immersed in the liquors, together with suitable circuitry, can be made to produce a temperature correction signal which may be applied, say, to the input circuitry of amplifier A2'.

A foul alarm FA is also arranged across the electrodes 14 of the measuring cell to indicate, by measurement of the constant current flow, when the actual fouling of the electrodes 14 reaches an unacceptable level.

Figure 4:
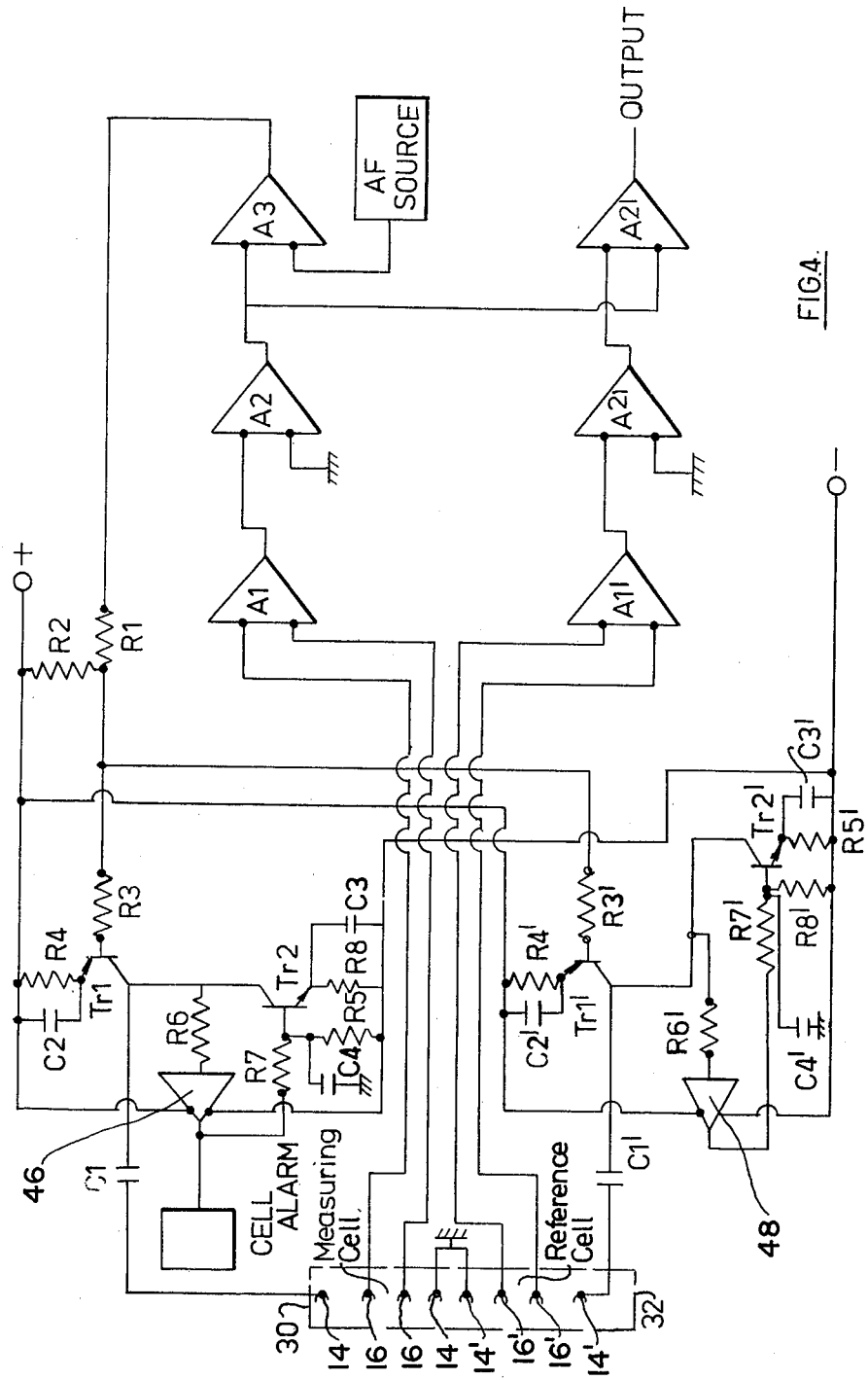
FIG. 4 shows a constant circuit diagram for use with the cell of the invention.

In the constant current circuit arrangement shown in FIG. 4 the inner electrodes 16 of the measuring cell are connected to the input terminals of a high impedance unitary gain amplifier A1 and the inner electrode 16' of the reference cell are connected to the input terminals of an amplifier A1', similar to amplifier A1. The output of amplifiers A1 and A1' are extended to input terminals of differential amplifiers A2 and A2' respectively and the other input terminals of the amplifiers A2 and A2' are extended to earth. Alternatively said other input terminals are used as inputs for reference or comparison purposes.

The output of amplifier A2 is connected to one input terminal of an amplifier A3, the other input terminal of amplifier A3 is connected to an A.F. source, the output of amplifier A2' is connected to one terminal of an amplifier A3' and the other input terminal of amplifier A3' is connected to the output of amplifier A2. The output of amplifier A3' may be used in identical manner to the amplifier A3' shown in FIG. 3 and the output of amplifier A3 constitutes the feedback for the constant current control circuit.

The Transistors TR1 and TR2 are complementary P.N.P. and N.P.N. types to form a current source of high impedance. A portion of the A.F. voltage at the output of A3 is applied, via the voltage divider R1,R2 to the base of transistor TR1, the resulting alternating current being defined by resistor R4 in the emitter circuit. Current sinking of the transistor TR1 collector circuit is performed by transistor TR2 with resistor R5 in the emitter circuit.

The network R6, amplifier 46, R7, and R8, provides D.C. feedback to maintain the mean voltage at the collectors of transistors TR1 and TR2 about earth potential, smoothing being provided by capacitor C4.

Amplifiers 46 and 48, are each connected across the positive-negative leads and the output from amplifier 46 prior to smoothing provides a suitable signal to operate the cell alarm circuit. The capacitors C2, C3 in the emitter circuit of transistors TR1 and TR2 correct for phase shift which can cause spurious oscillations. The alternating current output is fed to the electrode 14 of the measuring cell as shown in FIG. 4.

The transistor TR1' of the reference cell circuit receives an identical voltage to that applied to transistor TR1 and the reference cell circuit, as illustrated in FIG. 4, works in identical manner to the measuring cell circuit.

With the above arrangement, and in like manner to the arrangement shown in FIG. 3, the constant current, which is sensibly independent of the cell resistance, is fed to the measuring cell 30 and will adjust so that the voltage across electrode 16 remains sensibly constant in spite of the changes in the conductivity of the cell liquor. At the same time a second constant current of equal magnitude to that applied to the cell 30 is also applied to cell 32.

In this specification the term "high impedance" means an impedance in the order of 10 to 15 megohms.

In the example described with reference to FIGS. 3 and 4 the invention is utilized the relate to alkaline content of the liquid in the measuring cell to the normally lower alkaline content of the liquid in the reference cell. It will however be apparent to persons skilled in the art that the invention can be applied to relate the alkaline content of the liquid in the measuring cell to a normally higher alkaline content liquid in the reference cell whereby values for alkaline deficiency in the measuring cell liquid can be detected and measured.

We claim:

1. A method of comparing the electrical conductivity of two liquid samples propense to fouling electrodes in contact therewith, said method comprising the steps of introducing the sample to be tested into one cell and the sample to be used as a reference into another cell, each cell including four linearly aligned electrodes; applying an identical current to the outer electrodes of each of the cells; directly connecting the input of a first high input impedance amplifier to the inner electrodes of said four linearly aligned electrodes in said one cell, and the input of a second high input impedance amplifier to the inner electrodes of said four linearly aligned electrodes in said other cell, said amplifiers having an input impedance sufficiently high as to render the potential drops across said inner electrodes essentially independent of any fouling thereof by the liquid; varying the magnitude of said identical current applied to said outer electrodes of said cells in dependence upon the voltage across the inner electrodes of said one cell so as to maintain a constant predetermined voltage drop across said inner electrodes of said one cell; and comparing the output voltages of said first and second high input impedance amplifiers to provide a signal indicative of the difference in conductivity between the two liquid samples.

2. The method defined in claim 1 and including the further step of activating an alarm where a predetermined increased voltage appears across the electrodes of one of said cells.

3. The method defined in claim 1 and including the further step of amplifying said signal in a variable gain amplifier.

4. Apparatus for comparing the electrical conductivity of two liquid samples propense to fouling electrodes in contact therewith, said apparatus comprising:
   two cells, one for holding a sample to be tested, and the other to hold a reference sample, each cell comprising a housing for containing the liquid sample and four linearly aligned electrodes disposed in said housing;
   current source means connected to the outer electrodes of each cell for applying an identical current across the two outer electrodes of each cell;
   amplifier means, one for each cell, connected across the inner electrodes of said cell for providing an output dependent upon the voltage across the inner electrodes of said cell, said amplifier means each having an input impedance sufficiently high as to render the potential drop across said inner electrodes essentially independent of any fouling thereof by the liquid;
   varying means connecting the output of said amplifier means which is connected to said one cell to said current source means for varying the magnitude of said identical current in dependence upon the output of said amplifier means which is connected to said one cell so as to maintain a constant predetermined voltage drop across said inner electrodes of said one cell; and
   comparator means connected to the outputs of said amplifier means for comparing the output voltages of the two amplifier means to provide a signal indicative of the difference in conductivity between the liquid samples.

5. Apparatus as defined in claim 4, including an alarm connected across the outer electrodes of one of the cells and responsive to a predetermined increased voltage appearing across the latter outer electrodes.

6. Apparatus as defined in claim 4, further comprising a variable gain amplifier connected to the output of the comparator to receive and amplify said signal.

* * * * *